United States Patent [19]

Hotchkiss et al.

[11] Patent Number: 5,589,361
[45] Date of Patent: Dec. 31, 1996

[54] HUMAN TISSUE-TYPE PLASMINOGEN ACTIVATOR VARIANT

[75] Inventors: Adair J. Hotchkiss, Half Moon Bay; John V. O'Connor, San Carlos; Michael W. Spellman, San Bruno, all of Calif.

[73] Assignee: Genentech, Inc., San Bruno, Calif.

[21] Appl. No.: 581,189

[22] Filed: Sep. 10, 1990

Related U.S. Application Data

[63] Continuation of Ser. No. 118,098, Nov. 6, 1987, abandoned, which is a continuation-in-part of Ser. No. 21,893, Mar. 4, 1987, abandoned, which is a continuation-in-part of Ser. No. 841,075, Mar. 18, 1986, abandoned.

[51] Int. Cl.[6] ............................ A61K 38/49; C12N 15/58
[52] U.S. Cl. ............... 435/69.1; 435/226; 435/240.2
[58] Field of Search .................... 435/212, 226, 435/172.3, 320.1, 219; 935/10, 14

[56] References Cited

U.S. PATENT DOCUMENTS

| | | | |
|---|---|---|---|
| 4,753,879 | 6/1988 | Rosa et al. | 435/212 X |
| 4,766,075 | 8/1988 | Goeddel et al. | 435/212 X |
| 5,002,887 | 3/1991 | Larsen | 435/212 |
| 5,071,972 | 12/1991 | Larsen | 536/23.5 |
| 5,073,494 | 12/1991 | Heyneker | 435/226 |
| 5,106,741 | 4/1992 | Marotti et al. | 435/226 |
| 5,344,773 | 6/1994 | Wei et al. | 435/226 |

FOREIGN PATENT DOCUMENTS

| | | |
|---|---|---|
| 0178105 | 4/1986 | European Pat. Off. . |
| 0225286 | 6/1987 | European Pat. Off. . |
| 2173804 | 10/1986 | United Kingdom ............. 435/212 |
| WO84/01960 | 5/1984 | WIPO . |
| 8401786 | 5/1984 | WIPO ............................ 435/226 |
| 8704722 | 8/1987 | WIPO ............................ 435/212 |

OTHER PUBLICATIONS van Zonneveld, A. et al., *PNAS*, 83:4670–74, Jul. 1986.
Pennica, D. et al, *Nature*, vol. 301, pp. 214–221, 1983.
Pohl, et al, *Biochemistry*, vol. 23, pp. 3701–3707, 1984.
Zoller, et al, *Nuc Acids Res*, vol. 10, pp. 6487–6500, 1982.
Tate, K. et al, *Biochemistry*, vol. 26, pp. 338–343, Jan., 1987.
Little et al. (*Biochemistry* 23, 6191 (1984).

*Primary Examiner*—Marianne P. Allen
*Attorney, Agent, or Firm*—Walter H. Dreger

[57] ABSTRACT

Novel human tissue-type plasminogen activator variant that a) retains substantially full biological activity b) has a modified carbohydrate structure and c) has an altered in vivo half-life. Means for preparation of the variants and results of assays measuring function of the activators are also disclosed.

2 Claims, 7 Drawing Sheets

HUMAN TISSUE-TYPE PLASMINOGEN ACTIVATOR VARIANT

This application is a continuation of application Ser. No. 118,098, filed Nov. 6, 1987 now abandoned, which is a continuation-in-part of U.S. Ser. No. 07/021,893, filed Mar. 4, 1987, which in turn was a continuation-in-part of U.S. Ser. No. 06/841,075 filed Mar. 18, 1986, both now abandoned.

FIELD OF THE INVENTION

The present invention is directed to novel human tissue-type plasminogen activator variants modified in their carbohydrate structure and compositions thereof and to the means and methods for their production in therapeutically significant quantities.

BACKGROUND OF THE INVENTION

The present invention arises from the discovery that clearance of human tissue-type plasminogen activator from the circulation can be manipulated by altering the molecule's carbohydrate structure.

Tissue-type plasminogen activator (t-PA) is a serine protease that is involved in fibrinolysis. Binding of t-PA to a fibrin clot causes an enhancement of plasminogen activation (Hoylaerts, M. et al., *J. Biol. Chem.* 257:2912–2919 [1982]; Rijken, D. C., et al., *J. Biol. Chem.* 257:2920–2925 [1982]). Human tissue-type plasminogen activator converts plasminogen to plasmin. The plasmin, so produced, proteolytically cleaves fibrin matrices which comprise the backbone of blood clots. Human tissue-type plasminogen activator thereby mediates the dissolution of blood clots and is consequently useful in the treatment of various thrombolytic disorders. Although t-PA has been isolated from many sources such as the Bowes melanoma cell line (Rijken, D. C. et al., *J. Biol. Chem.* 256:7035–7041 [1981]; Wallen, P., et al., *Eur. J. Biochem.* 132:681–686 [1983]), uterine tissue (Rijken, D. C. et al. *Biochim. Biophys. Acta* 580:140–153 [1979]) and blood vessel perfusates (Binder, B. R., et al., *J. Biol. Chem.* 254:1998–2003 [1979]), the advent of recombinant DNA technology has allowed the production of t-PA (Pennica, D. et al., *Nature* (London) 301:214–221 [1983]) in sufficient quantities to perform clinical trials on patients with myocardial infarction, peripheral vascular thrombi and pulmonary embolism. These trials have shown that recombinant t-PA (rt-PA) is an extremely effective thrombolytic agent with minimal effects on fibrinogen levels in the blood (Williams, D. O., et al., *Circulation* 73:338–346 [1986]; Graor, R. A. et al., *Circulation* 74(suppl.1):1-15-1-20 [1986]; Collen, D., et al., *Circulation* 73:511–517 [1986]).

The elimination of rt-PA from the circulation is relatively rapid. The biphasic clearance is dominated by an alpha phase with a half life of about 2 min in rabbits (Korninger, C., et al., *Thromb. Haemos.* 46:658–661 [1985]; Nilsson, S., et al., *Thromb. Res.* 39:511–521; Bounameaux, H., et al., *Blood* 67:1493–1497 [1986]) and 4 min (Baughman, R. A., *Tissue Plasminogen Activator in Thrombolytic Therapy* (Sobel, et al., eds.) pp. 41–53, Marcel Dekker, N.Y. [1987]) to 6 min (Wallen, P. et al., supra) in humans. The liver is the most significant site of t-PA uptake and metabolism (Korninger, C., et al., supra; Nilsson, S., et al., supra; Bounameaux, H., et al., supra). A number of receptor systems in the liver have been described which recognize specific terminal residues on the oligosaccharide portions of glycoproteins. Proteins cleared by this mechanism also have half lives on the order of a few minutes (Ashwell, G. et al., *Ann. Rev. Biochem.* 51:531–554 [1982]).

Recombinant t-PA has four potential sites for N-linked glycosylation. A high mannose oligosaccharide is present at position 117 and a complex oligosaccharide at position 448. At position 184 a complex oligosaccharide is present in type I rt-PA and absent in type II rt-PA; the ratio of type I to type II is about 1 to 1. A fourth potential glycosylation site at residue 218 is not glycosylated. The glycosylation pattern of rt-PA is similar to that of melanoma-derived t-PA.

The abbreviation t-PA for human tissue-type plasminogen activator was adopted after proposal at the XXVIII Meeting of the International Committee on Thrombosis and Hemostatis, Bergamo, Italy, 27 Jul. 1982. As used herein, the terms "human tissue-type plasminogen activator", "t-PA", "human t-PA" or "tissue plasminogen activator" denote human extrinsic (tissue-type) plasminogen activator, produced, for example, from natural source extraction and purification [see Collen et al., European Patent Application No. 41766 (published 16 Dec. 1981 based upon a first filing of 11 Jun. 1980) and Rijken et al., *Journal of Biol Chem.* 256, 7035 (1981), incorporated herein by reference, and by recombinant cell culture systems as described together with its amino acid sequence and physical and biological characteristics, for example, in European Patent Application Publication No. 93619, (published 9 Nov. 1983) based upon a first filing of 5 May 1982), incorporated herein by reference.

U.S. Pat. No. 4326033 reports extending the half-life of urokinase by chemically modifying its carbohydrate structure. Urokinase is immunologically distinct from human tissue-type plasminogen activator. There is no justification, either from U.S. Pat. No. 4,326,033 or otherwise, in considering that such carbohydrate modifications of urokinase would have applicability to other glycoproteins. Indeed, for example, removal of sialic acid from ceruloplasmin decreases its half-life dramatically; yet, identical treatment of transferrin, another serum glycoprotein, has no significant effect on half-life. (Sharon, *Complex Carbohydrates*, Addison-Wesley Publ. Co., p. 194–196, (1975); see also Ashwell et al., *Adv. Enzymology* 41, 99 (1974) and Alexander et al., *Science* 226, 1328 (1984).

The elimination of melanoma-derived t-PA in mice has been reported to be unaffected by titration of the active site with phenylmethylsulfonyl fluoride or by the coinjection of diisopropylfluorophosphate thrombin, asialoorosomucoid, macroalbumin or excess unlabeled t-PA (Fuchs, H. E., et al. *Blood* 65:539–544 [1985]). The results obtained with asailoorosomucoid and macroalbumin would indicate that carbohydrate structures do not influence the clearance of t-PA. The clearance of melanoma derived t-PA has been reported to be unaffected by monosaccharides in rats (Emeis, C. M., et al., *Thromb. Haemos.* 54:661–664 [1985]). On the other hand, when the cellular components of the rat liver were separated, the endothelial cells were reported to take up melanoma t-PA by a pathway that could be inhibited by high mannose glycoproteins; this result was interpreted to mean that t-PA is taken up into the liver at least in part by the mannose receptor (Einarsson, M., et al., *Thromb. Haemos.* 54:270 [1985]). In other in vitro studies, rt-PA was shown to bind with high affinity to rat liver hepatocytes. The receptor did not appear to be carbohydrate-dependent (Bakhit, C., et al., *J. Biol. Chem,* 262:8716–8720 [1987]).

In Patent Application International Publication No. WO84/01786, published 10 May 1984 based upon a first filing of 28 Oct. 1982, there is described an indiscriminate modification of tissue-type plasminogen activator resulting in a molecule with reduced biological activity and purported increased half-life, compared with the unmodified polypeptide. The single example involves treating a partially purified human tissue-type plasminogen activator with sodium periodate giving a product reported to have about 70 to 90 percent of the original (unmodified) activity. There is no indication in WO84/01786 of an appreciation of the nature and characterization of the carbohydrate structures present in native material, and more importantly, in the modified form they produce. In fact, periodate is known to modify or disrupt, by oxidation, all carbohydrate structures without their concomitant, substantial removal from amino acid linkage.

There is also no indication in WO84/01786 of how many such structures human tissue-type plasminogen activator has, or what the actual carbohydrate make-up is, either for unmodified or their modified version. Thus, their periodate treated molecule was most probably modified by oxidation of all carbohydrate structures indiscriminately, without focus on a particular site.

Recently, it was reported that the in vivo clearance rates of glycosylated and deglycosylated human tissue-type plasminogen activator were not significantly different, forcing the conclusion that the clearance rate of human tissue-type plasminogen activator is not affected by the absence of carbohydrates (Larsen et al., *Proteases in Biological Control and Biotechnology*, UCLA Symposium Park City, Utah,. Feb. 9–14, 1986. See Little et al., *Biochemistry* 23, 6191 (1984).

It is an object of the present invention to provide novel t-PA variants by modifying its carbohydrate structure. Another object of this invention is to provide t-PA variants that can be cleared from the circulation at different rates. Yet another object of this invention is to provide effective thrombolytic agents suitable for treatment of diverse clinical conditions.

SUMMARY OF THE INVENTION

The objects of this invention are accomplished by novel tissue-type plasminogen activator variants modified in their carbohydrate structure, that retain substantially full biological activity and have an altered in vivo half-life, i.e. are cleared from the circulation at a rate different from that of naturally occurring t-PA. In particular, the t-PA variants are modified in their carbohydrate structure at positions 117, 184 or 448. It was not appreciated until this invention that alteration of the carbohydrate structure of t-PA could alter its clearance from the circulation. In particular, this invention established that carbohydrate elimination from one or more of the glycosylation sites of t-PA will prolong t-PA half-life. In particular, this invention also established for the first time that a t-PA variant having high mannose oligosaccharides at positions 184 and 448 in addition to that present at position 117 will be cleared from the circulation more quickly.

The present invention is thus directed to novel human tissue-type plasminogen activators devoid of functional carbohydrate structure at amino acid residue 117, otherwise having functionally unmodified carbohydrate structures (at amino acid residues 184 and/or 448), and having retained substantially full biological activity and increased in vivo half-life (compared with "native" human tissue-type plasminogen activator having an intact carbohydrate structure at amino acid residue 117).

The present invention is also directed to a novel human tissue-type plasminogen activator variant devoid of functional carbohydrate structure at positions 117, 184 and 448, and having retained substantially full biological activity and increased in vivo half-life (compared with "native" human tissue-type plasminogen activator having intact carbohydrate structure at those positions).

The present invention is also directed to a novel human tissue-type plasminogen activator variant having substituted high mannose oligosaccharide at positions 184 and 448 in addition to that present at position 117, and having retained substantially full biological activity and a reduced half-life (compared with "native" human tissue-type plasminogen activator having intact unmodified carbohydrate structure at positions 184 and 448).

The present invention is further directed to biologically active human tissue-type plasminogen activator equivalents differing in one or more amino acid(s) in the overall sequence but having the same carbohydrate pattern as the particular novel human tissue-type plasminogen activator variants hereof. The present invention is further directed to associated recombinant vectors, cultures, and methods useful for preparing the novel human tissue-type plasminogen activator variants hereof.

One such human tissue-type plasminogen activator variant equivalent included within the scope hereof is a so-called single-chain mutant wherein the cleavage site between amino acids 275 and 276 is destroyed by eliminating the amino acid sequence recognized by proteolytic enzymes. The elimination of the sequence is effected by changing specific amino acids, for example, by site-specific mutagenesis of the underlying DNA codons according to the method described infra.

DETAILED DESCRIPTION

General

It has been found that the carbohydrate structure at amino acid residue 117 of human tissue-type plasminogen activator has the following type of composition:

while the structures at amino acid residues 184 and 448 have the following types of compositions:

Abbreviations: Man - mannose; Gal - galactose; Fuc - fucose; GlcNAc - N acetylglucosamine; Sia - sialic acid; R - H or Sia2→3Gal→4GlcNAc.

It should be emphasized that, while the above structures are representative of the types of N-linked oligosaccharides found on human tissue-type plasminogen activator, the present invention is not limited to the structures shown. Each glycosylation site probably contains several closely related, non-identical structures. This is known as microheterogeneity and is a common characteristic of glycoprotein glycans [See *J. Biol, Chem.* 260, 4046 (1985)]. For example, high-mannose oligosaccharides can vary in the number of mannose units present. In complex oligosaccharides, microheterogeneity can involve differences in the extent of branching as well as in the number of residues of sialic acid, fucose, galactose and N-acetylglucosamine. Such microheterogeneity is intended to be within the scope of the present invention.

The high-mannose containing structure at amino acid 117 proved unique, not only in structure from the more complex structures at amino acid residues 184 and 448, but also in that its complete functional removal without concomitant functional modification of the structures at 184 and 448 resulted in a fully biologically active human tissue-type plasminogen activator having increased in vivo half-life.

Removal of functional carbohydrate structure at amino acid residue 117 means complete removal, as where the glycosylation signal is destroyed by site-directed mutagenesis as described infra, or substantial removal, as by treatment with endoglycosidase which may leave an intact N-acetylglucosamine residue linked to $Asn_{117}$, or substantial removal at positions 117, 184 and 448 by treatment with sodium periodate which oxidizes vicinal hydroxyl groups, for example. Functionally unmodified carbohydrate structure at amino acid residues 117, 184 and/or 448 means either retention of the intact structure(s) or substantially all of such structure(s) such that they are functionally equivalent to native protein.

Alteration of the carbohydrate structure at amino acids 184 in type I recombinant t-PA and 448 means substitution of a high mannose oligosaccharide for the complex oligosaccharide by production of the recombinant tissue-type plasminogen activator in a host cell lacking the enzyme N-acetylglucosamine transferase which converts a high mannose oligosaccharide to a complex oligosaccharide. This high mannose t-PA variant resulted in a substantially full biologically active human tissue-type plasminogen activator variant having a reduced in vivo half life.

In a preferred embodiment, removal of functional carbohydrate structure at amino acid residue 117 is accomplished by site-specific mutagenesis of the underlying DNA of the glycosylation signal Asn-X-Ser/Thr, where X can be any amino acid. In the case of tissue-type plasminogen activator, the sequence representing this signal is $Asn_{117}$ ($Ser_{118}$) $Ser_{119}$. Removal of functional carbohydrate structure at amino acid residue 117 thus results, for example, by mutagenizing the codons corresponding to these amino acid residues, destroying the signal functionality. In particular, mutagenesis can be performed on representative codons of the signal such that there is produced, for example, a human tissue-type plasminogen activator having an amino acid residue other than asparagine (Asn) at position 117 and/or other than serine (Ser) or threonine (Thr) at position 119 or a proline (Pro) at position 118. In a most preferred embodiment, asparagine 117 is replaced with glutamine, in view of their close structural similarity, or $serine_{119}$ is replaced with methionine, in view of an analogous sequence in the second kringle region.

The mutagenesis is accomplished via techniques known per se, for example, according to the methods reviewed by Zoller et al., *Methods in Enzymology* 100, 468 (1983). For example, by changing the asparagine encoding codon AAC at position 117 with CAA or CAG, requiring two nucleotide changes, the expression product will contain glutamine at position 117. Other mutations contemplated herein follow from analysis of the genetic code.

An alternative method of functional carbohydrate removal at amino acid residue 117 involves the use of an endoglycosidase such as Endoglycosidase H which is capable of (substantially) removing the high mannose carbohydrate structure at amino acid residue 117 (Asn) without functionally affecting the complex structures at amino acid residues 184 and 448. Again, this treatment is accomplished via techniques known per se, for example, according to the method of Tarentino et al., *J. Biol. Chem.* 9, 811 (1974) and Trimble et al., *Anal. Biochem.* 141, 515 (1984).

Another method of functional carbohydrate removal at amino acid residues 117, 184 and 448 is by treatment with sodium periodate, accomplished by techniques known per se, which oxidizes carbohydrate residues that contain vicinal hydroxyl groups. The oligosaccharides at all three positions 117, 184 and 448 contain residues susceptible to periodate oxidation.

Yet another method of altering the carbohydrate structure by changing the complex oligosaccharide at positions 184 in type I recombinant t-PA and 448 to a high mannose oligosaccharide using recombinant techniques as, for example, transfecting a host cell lacking the enzyme necessary for synthesis of complex type N-linked oligosaccharides (Gottlieb, C. et al. *J. Biol, Chem,* 250: 3303–3309 [1975]) with an expression vector encoding t-PA.

The following examples merely illustrate the best mode now known for practicing the invention, but should not be construed to limit the invention. All literature citations herein are expressly incorporated by reference.

EXAMPLE 1 t-PA Carbohydrate Variant $Gln_{117}$ Lacking

High-Mannose Oligosaccharide at Position 117

Site specific mutagenesis was used to construct an expression vector capable of expressing DNA encoding tissue-type plasminogen activator having amino acid residue glutamine at position 117 rather than an asparagine, as follows:

A. Oligonucleotide Design

A 24-mer oligonucleotide having the sequence 5'-TGC-ACC-AAC- TGG-C*A*A*-AGC-AGC-GCG-3' (24-mer Q117) was synthesized by the phospho-triester method of Crea et al., *Nucleic Acids Research* 8, 2331 (1980). Asterisks indicate the mutant (asn to gin) codon.

B. Construction of Recombinant M13 Template

Figure 3:
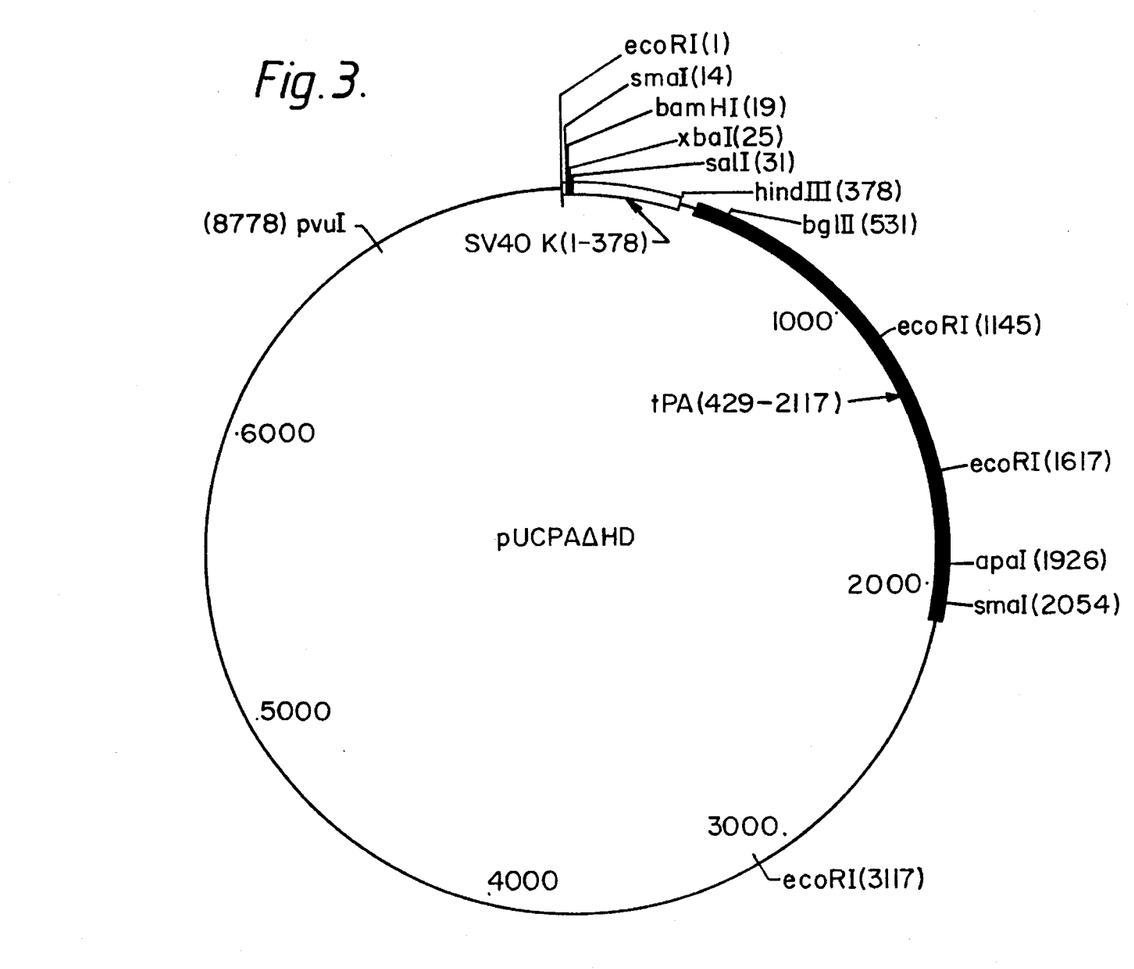
FIG. 3 represents a restriction map of starting plasmid pUCPAΔHD.

Plasmid pUCPAΔHD (FIG. 3) is a derivative of plasmid designated pETPFR (otherwise designated pPADHFR-6 disclosed in EPO 93619, supra.), with the following modifications: 1) 166 b.p. of 5' untranslated DNA has been trimmed from the 5' end of the t-PA gene, using exonuclease Bal 31; 2) a Hind III site has been added to the new 5' end of the t-PA gene; 3) a polylinker, containing recognition sites for EcoR1, Sac I, Sma I, Bam HI, Xba I, Sal I, and Pvu II, has been added to the 5' end of the SV40 early promoter that drives t-PA expression; 4) the Hind III site at position 3539 of pETPFR has been destroyed by a Klenow fill-in reaction.

Plasmid pUCPAAHD (FIG. 3) was digested with SmaI, and the ca. 2.0 kb fragment containing the t-PA gene through codon No. 507 was isolated by PAGE and electroelution of the fragment from the gel. M13mp10 (Messing, *Methods in Enzymology* 101, 20 (1983) vector was also digested with SmaI, extracted once with phenol, chloroform, ethanol precipitated, and resuspended in 50 mMtris pH8.0, 1mMEDIA (TED. The ca. 2.0 kb fragment from pUCPAΔHD was ligated into the SmaI cut M13mp10 using T4 DNA ligase and the resulting DNA was used to transform *E. coli* JM101. The resulting phage was isolated and the presence of the insert was verified and its orientation determined by restriction analysis of phage minipreps. One recombinant phage, M13/t-PA-SMA, was chosen as template for subsequent mutagenesis.

C. Mutagenesis Reaction

The mutagenesis primer (24-mer Q117) was annealed to single-stranded M13/t-PA-SMA DNA, and treated with *E. coli* DNA polymerase Klenow fragment in the presence of dNTPs and T4 DNA ligase to create in vitro heteroduplex RF molecules, as described by Adelman et al., *DNA* 2, 183 (1983). These molecules were used to transform *E. coli* strain JM101 (ATCC No. 33876) and phage incorporating the desired mutation were detected by plague hybridation using the mutagenesis primer as a probe. (Adelman et al., *DNA* 2, 183 (1983). One mutant phage was isolated and designated M13/t-PA-SMA-GLN117.

D. Subcloning the GLN117 t-PA Mutant into Expression Plasmid pUCPAΔHD

Double stranded DNA of Phage M13/t-PA-SMA-GLN117 was digested with SmaI, BglII and ApaI and the ca 1.4 kb fragment purified by PAGE. This fragment was then used to replace the corresponding fragment in pUCPAΔHD.

Recombinant plasmids containing the t-PA gene fragment were identified. Plasmids M119 and Q117 are introduced into and amplified in DHFR deficient CHO cells (Urlab et al., *Proc. Natl. Acad. Sci.* 77, 4216 (1980) as follows: 1) plasmid DNA is introduced into the cells by the calcium phosphate precipitation method of Graham et al., *J. Virol.* 52, 455 (1973); 2) colonies arising in selective medium [medium lacking hypoxanthine, glycine, and thymidine (-HGT) are assayed for t-PA expression indirectly by detecting plasmin formation as assessed by the digestion of fibrin in an agar plate containing fibrin and plasminogen, described by Granellia et al., *J. Exp. Med.* 148, 223 (1978); 3) five of the most strongly positive clones are assayed quantitatively for the amount of t-PA secreted per cell using an ELISA assay; 4) the clone secreting the highest level of t-PA is plated into methotrexate (MTX) as follows: $2 \times 10^5$ cells are plated into 100 mm plates containing 50, 100, or 250 nM MTX; 5) five clones arising in MTX are extracted and assayed quantitatively (by ELISA) as in Step 3) above; 6) the clone secreting the highest level of t-PA is plated into higher concentrations of MTX as in Step 4) above, followed by quantitative assay of five clones that arise, and selection of the highest t-PA producer.

The above amplification and screening procedure is repeated until no increases in t-PA production are obtained from the resulting cell line and the corresponding mutant t-PA is separated for use.

EXAMPLE 2 t-PA Carbohydrate Variant $Met_{119}$ Lacking
High-Mannose Oligosaccharide at Position 117

N-linked glycosylation at position 117 requires an Asn-X-Ser/Thr sequence to take place. Substitutional or deletional mutagenesis at position 119 will also prevent glycosylation at position 117. A similar procedure as that described in Example 1 was used to make the corresponding $Met_{119}$ mutant using a 24-mer with the sequence 5'-CC-AAC-TGG-AAC-AGC-A*T*G*-GCG-TTG-G-3' (24-mer M119) to give pUCPAΔHD M119. Production of the corresponding M119 mutant by expression is as described above in Example 1.

EXAMPLE 3 t-PA Carbohydrate Variant $Gln_{117}Glu_{275}$ Equivalent

A glutamine$_{117}$ glutamic acid$_{275}$ t-PA mutant was prepared as follows:

Plasmid pUCPAΔHD, prepared as described above, was digested with Bgl II and Sca I and the about 763 bp fragment, corresponding to codons 1 to 254 of the tissue-type plasminogen activator DNA sequence, was purified on SDS-PAGE in a manner known per se.

Human t-PA DNA was obtained from plasmids pPADHFR-6 (also designated pETPFR) and pA25E10. The preparation of these two t-PA plasmids is described in European Patent Application Publication No. 093619, corresponding to U.S. Pat. No. 4,766,075, referred to above and incorporated herein by reference.

Plasmid pA25E10 contains sequences coding for the last 508 amino acids of the t-PA gene and 772 base pairs of the 3' untranslated region. This plasmid was digested with SacI and BglII to produce a 744 base pair fragment which was isolated by standard methods as previously described. This fragment contains the codons for t-PA amino acids 411 through 527 and includes part of the 3'untranslated region.

Plasmid pPADHFR-6 contains the entire structural gene for t-PA and part of the 3' untranslated region. This plasmid was digested with SacI and BglII to produce a 1,230 base pair fragment which was isolated. This fragment contains codons for the first 410 amino acids of the mature form of t-PA.

These fragments were ligated together using standard methods and digested with BglII. A 1,974 base pair fragment containing codons for the entire mature t-PA sequence plus part of the 3' untranslated region was isolated. Double stranded M13mp8, [Messing et al., Third Cleveland Symposium on Macromolecules Recombinant DNA, Editor A. Walter, Elsevier, Amsterdam (1981), p. 143] was digested with BamHI and annealed to the BglII digested t-PA to form M13mp8PABglII. E. coli JM 101 cells (ATCC No. 33876) were transformed with the double stranded replicative form of M13mp8PABglII. The single stranded and double stranded (RF) forms of M13mp8PABglII may be isolated from E. coli JM 101 cells infected with this phage. The single stranded form was used for the site specific mutagenesis of t-PA.

The human t-PA structural gene was modified by site specific mutagensis to express t-PA with amino acid substitutions at various positions. A synthetic oligonucleotide was prepared such as by the solid phase phosphotriester method of Crea et al., *Proc. Natl. Acad. Sci.* (USA) 75, 5765 (1978) and used for such site specific mutagenesis:

```
Primer 2C9              Glu
DNA Sequence   G CCT CAG TTT GAA ATC AAA GGA G
```

The general method of Adelman et al., *DNA* 2, 183 (1983), incorporated herein by reference, was used to generate a t-PA clone containing the mutated sequence of the synthetic primer. Mutant t-PA clone M13RF2C9 was generated by the use of the primer containing the mutation for the single amino acid shown above.

In the plasmid pPADHFR-6 (also designated pETPFR—see European Patent Application Publication No. 93619 supra) the expression of the native t-PA structural gene is under the control of the early promoter for SV40 T-antigen. This promoter also controls the expression of the DHFR gene. A vector Fragment 1 was obtained by isolating the large fragment generated by digestion of pPADHFR-6 with BglII and BstEII. Another Fragment 2 was obtained by isolating the 400 base pair t-PA fragment obtained from the digestion of pPADHFR-6 with BglII and BstXI. A 1,141 base pair t-PA fragment 3 containing the desired mutation was obtained by digesting RF DNA from mutant t-PA clone M13RF2C9 with BstXI and BstEII. Fragments 1 and 2 were ligated with Fragment 3. The DNA mixture was used to transform E. coli to give eukaryotic expression vector pPADHFR-6 2C9.

Plasmid pPADHFR-6 2C9, prepared as described above and in European Patent Application Publication No. 199574, published 29 Oct. 1986, contains a DNA sequence encoding glutamic acid 275 tissue-type plasminogen activator mutant. It was digested with Sca I and Apa I and the about 630 bp fragment, corresponding to codons 254 to 466 of the tissue-type plasminogen activator DNA sequence, was purified on SDS-PAGE in a manner known per se.

The two BglII-ScaI (pUCPAΔHD) and ScaI-ApaI (pPADHFR-6 2C9) fragments were ltgated into the large Bgl II (bp 531) - Apa I (1926 bp) fragment from digested pUCPAΔHD and the resultant plasmid harboring glutamine$_{117}$ glutamic acid$_{275}$ t-PA mutant DNA was miniscreened in the usual manner. The resultant plasmid was introduced into and amplified in DHFR deficient CHO cells as described above and the corresponding mutant t-PA was separated for use.

EXAMPLE 4

Characterization of t-PA Carbohydrate Structure

The amino acid sequence of t-PA includes 4 potential N-linked glycosylation sites [Asn-X-Ser/Thr; *Ann, Rev. Biochem.* 41, 673 (1972)]. These are asparagine residues 117, 184, 218 and 448 [*Nature* 301, 214 (1983)]. Position 218, however, has been found not to be glycosylated in t-PA. Position 184 is glycosylated in type I t-PA but not in type II t-PA [*Biochemistry* 23, 3701 (1984)].

Gel-filtration chromatography of Pronase-digested rt-PA resolved two classes of N-linked oligosaccharides (Table 1 below). The composition of the higher molecular weight material was consistent with fucosylated complex-type oligosaccharides. The lower molecular weight material had the expected composition for a small high-mannose oligosaccharide (probably Man$_6$GlcNAc2).

The attachment position of the high-mannose oligosaccharide was determined by utilizing glycosidic enzymes of different specificities. The enzymes used were endo-β-N-acetylglucosaminidase H (Endo H; Genzyme, Inc.), that removes high-mannose oligosaccharides but has no effect on complex-type oligosaccharides, and peptide-N-glycosidase F (N-glycanase; Genzyme, Inc.), that removes both high-mannose and complex-type oligosaccharides. The t-PA used for these experiments had been converted to the two-chain form with plasmin and then reduced and carboxymethylated.

Figure 2:
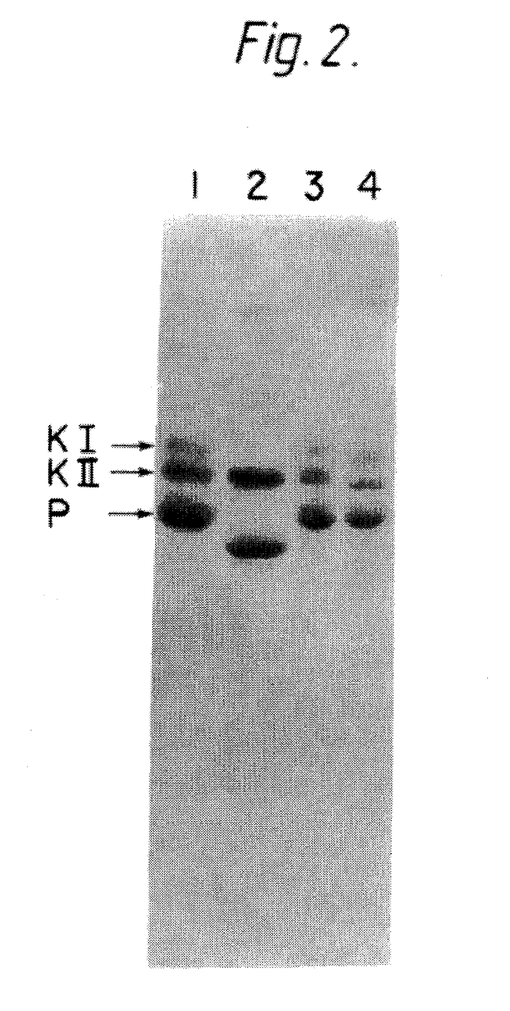
FIG. 2 represents glycosidase digestions of reduced carboxymethylated t-PA. Lane 1: −N-glycanase; Lane 2: +N-glycanase; Lane 3: −Endo H; Lane 4: +Endo H. Band identifications as in FIG. 1.

SDS-PAGE resolves reduced carboxymethylated two-chain rt-PA into type I kringle (glycosylation at 117 and 184), type II kringle (glycosylation at 117) and protease (glycosylation at 448). N-glycanase digestion of t-PA causes the kringle bands to coalesce at a position of slightly greater mobility than type II kringle and also causes increased mobility of the protease (lane 2, FIG. 2). Endo H digestion of t-PA increases the electrophoretic mobility of each kringle band, but does not affect the mobility of the protease band (lane 4, FIG. 2). The endo H result indicates that type I and type II kringle each contain a high-mannose oligosaccharide; this must be located at residue 117, which is the only position glycosylated in both type I and type II kringles. Endo H treatment does not convert type I to type II kringle; therefore, residue 184, which is glycosylated in type 1 but not in type II kringle, contains a complex oligosaccharide. Position 448 must also contain a complex structure, because N-glycanase treatment increases the mobility of the protease portion of rt-PA, while endo H has no effect.

TABLE I

Carbohydrate Composition of Oligosaccharide Fractions From Pronase-Digested t-PA

| Sample | Fuc | Man | Gal | GlcNAc | Sia[b] |
|---|---|---|---|---|---|
| Complex Type[c] | 1.0 | 3.0 | 2.8 | 4.2 | 2.4 |
| High-mannose Type[d] | 0.6 | 6.2 | trace | 2.0 | 0 |

Abbreviations:
Fuc = Fucose,
Man = Mannose,
Gal = Galactose
GlcNAc = N-acetylglucosamine,
Sia = sialic acid
[b]Thiobarbituric acid assay
[c]Normalized to 3 Mannose
[d]Normalized to 2 GlcNAc

EXAMPLE 5

Endo H Treatment t-PA

Endo-β-N-acetylglucosaminidase H (Endo H) was purchased from Genzyme, Incorporated. Endo H removes N-linked oligosaccharides of the high mannose type, but does not affect complex oligosaccharides. SDS-PAGE was performed as described by Laemmli, *Nature* 227, 680 (1970). 0.8 mg of human tissue-type plasminogen activator (prepared as described in EPA 93619, supra.) (in 0.2 ml formulation buffer consisting of 0.2 M arginine phosphate, pH 6, containing 0.01% Tween 80) was mixed with Endo H (0.1 unit in 0.05 ml of 25 mM sodium phosphate, pH 6) and sodium azide (0.02 percent). The sample was incubated at 37 degrees for 20 hours. A control human tissue-type plasminogen activator sample was prepared and incubated in the same manner except that sodium phosphate buffer (0.05 ml of 25 mm) was substituted for the Endo H solution. After incubation, the samples were diluted to a total volume of 0.75 ml with formulation buffer and extensively dialyzed into the same formulation buffer. The samples were filtered (0.4 micron HV filters, Amicon) and stored at 4 degrees.

Deglycosylation was monitored by SDS-PAGE after reduction and carboxymethylation. Aliquots of the thus prepared human tissue-type plasminogen activator (0.05 mg in 0.01 ml formulation buffer) were mixed with 25 mM sodium phosphate pH 6 (0.015 ml) and 2× Laemmli sample buffer containing 20 mM dithiothreitol (0.025 ml). The samples were heated for 5 minutes at 95 degrees and allowed to cool. Iodoacetic acid (0.015 ml of a 0.67M solution in 1N $NH_4OH$) was added and the samples incubated in the dark for 3 hours at room temperature. The reduced carboxymethylated samples were analyzed by SDS-PAGE.

Figure 1:
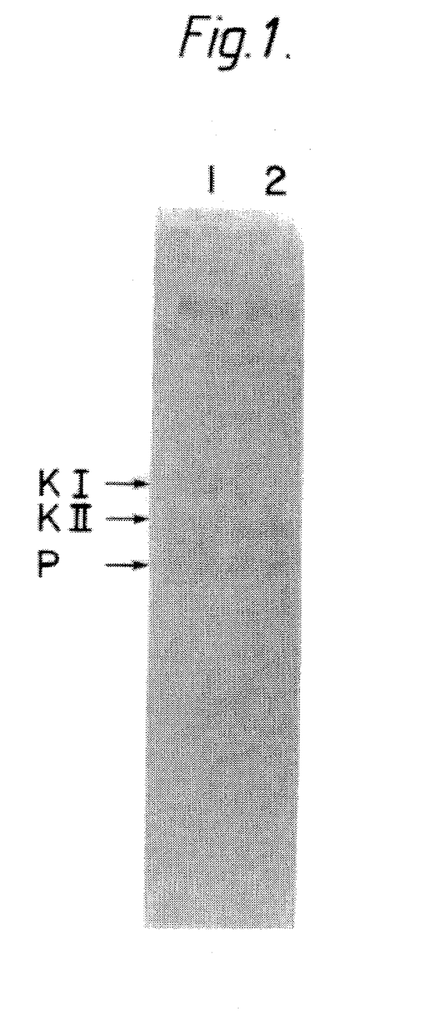
FIG. 1 represents a Comassie-stained SDS-PAGE of untreated (Lane 1) and Endo H treated (Lane 2) human tissue-type plasminogen activator. The high molecular weight band is 1-chain t-PA; the other major bands are type I Kringle (KI), type II Kringle (KII) and protease (P).

In this analysis, untreated control 2-chain human tissue-type plasminogen activator is resolved into three major bands, corresponding to type I kringle (glycosylation at positions 117 and 184), type II kringle (glycosylation at position 117), and protease (lane 1, FIG. 1). Endo H digestion of human tissue-type plasminogen activator increases the electrophoretic mobility of each kringle band, but does not affect the mobility of the protease band (lane 2, FIG. 1). The neutral and amino sugar composition of Endo-H treated t-PA is shown in Table 2. Endo H treatment reduced the mannose content by 5.6 residues per mole and the N-acetylglucosamine content by 0.9 residue per mole. This result is consistent with stoichiometric removal of the high mannose oligosaccharide from position 117.

The fibrinolytic activity of Endo H-treated human tissue-type plasminogen activator was assayed by the in vitro clot lysis assay of Collen et al., *J. Clin. Path.* 21, 705 (1968). The activity of Endo H-treated human tissue-type plasminogen activator was indistinguishable from that of the untreated control in this assay.

The human tissue plasminogen samples were iodinated by the Iodobead procedure [Markwell, *Anal. Biochem.* 125, 427 (1982)] to a specific activity of approximately 2 µCi/µg. Arginine, 0.2M, and citrate, 0.1M, (pH 6.0) and Tween 80, 0.01 percent, was the buffer used at all times. All samples were dialyzed into this buffer prior to iodination. pH was adjusted to 8.2 with Tris base prior to iodination. The iodination mixture was passed across a PD-10 column (Pharmacia) equilibrated with pH 6.0 buffer, the radioactive fractions from the void volume were pooled, SDS-PAGE was run and the dried gel was autoradiographed. Autoradiography of the labeled human tissue-type plasminogen activators showed that more than 95 percent of the radioactivity was incorporated into human tissue-type plasminogen activator.

Each labeled human tissue-type plasminogen activator was mixed with unlabeled material in a ratio of 1:200 (labeled: unlabeled, w/w) and injected i.v. as a bolus into rabbits that had an arterial catheter in the ear. Each rabbit received 1 mg/kg of unlabeled and 10 µCi/kg of labeled human tissue-type plasminogen activator. The unlabeled human tissue-type plasminogen activator was used as a carrier for the trace amount of labeled human tissue-type plasminogen activator in order to achieve therapeutic levels and to avoid alterations in the pharmacokinetics that could arise from concentration dependence in the clearance pathways. Serial arterial blood samples were collected over a 26 minute period and placed immediately into tubes containing a lyophilized mixture of D-phe-pro-arg-chloromethylketene (PPACK) and EDTA at final concentrations of 1 µM and 4.8 mM, respectively. The tubes were placed on ice and plasma was separated. Trichloroacetic acid (TCA) precipitable (intact human tissue-type plasminogen activator) and total radioactivity were measured in each plasma sample. The immunoreactive human tissue-type plasminogen activator was also measured by a sandwich ELISA procedure which utilized polyclonal antibodies and had an effective sensitivity of at least 30 ng/ml.

The plasma concentration time course data were fit to a two compartment model for bolus injection using an interactive curve stripping procedure[b] which uses the method of residuals (Gibaldi, M. et al., *Pharmacokinetics*, 2 nd ed., N.Y., Marcel Dekker, Inc., pp. 433–444 [1982]). The following exponential equation was used: $Cp = Ae^{-\alpha t} + Be^{-\beta t}$, where Cp is the concentration of rt-PA in the plasma at any time, t and A and B are the y intercepts of the fast and slow clearance phases which have slopes of α and β, respectively. The $t_{1/2}$ for the α and β phases were calculated as the ratio: ln2/slope. The results from the curve stripping procedure were used as initial approximations to fit the data to a biexponential model using PC NONLIN. One data set (FIG. 4) could not be fit using PC NONLIN so the data from the curve stripping procedure were used. $C_o$, the plasma concentration at zero time, was the sum of A and B. $V_o$ was calculated as dose divided by $C_o$. Area under the curve (AUC) was determined by formula AUC=A/α+ B/β. In every case the extrapolated area was less than 20% of the total AUC. AUC was then used to calculate the clearance using the formula, Clearance=$_{AUC}/^{Dose}$. The relative contributions of the alpha and beta phases were calculated from the following formulas:

$$\% AUC\alpha = \frac{A/\alpha}{AUC} \times 100$$

$$\% AUC\beta = \frac{B/\beta}{AUC} \times 100$$

The data for Table 2 were fit to a model with direct elimination from the central compartment ($K_{10}$) and equilibration with a peripheral compartment ($K_{12}$ and $K_{21}$).

Two types of data were generated from in vivo clearance studies in rabbits. One is from the immunoreactive human tissue-type plasminogen activator which should be a measure of the clearance of the unlabeled material. The second type of data is the TCA precipitable radioactivity, which represents more than 95 percent intact human tissue-type plasminogen activator. The curves of plasma concentration versus time from the immunoreactivity and the TCA precipitable counts were fit to the appropriate multiexponential models and the derived pharmacokinetic parameters were compared.

EXAMPLE 6

Periodate Treated rt-PA

Recombinant t-PA (1 mg/ml in 0.2M arginine phosphate buffer, pH 6) was cooled in an ice bath. Sodium periodate was added to a concentration of 10 mM and the mixture was kept in the dark for 1 hour at 4° C. Glycerol (100 mM) and ethanolamine (50 mM) were added to quench the reaction. The sample was then dialyzed exhaustively against pH 6 arginine phosphate buffer, filtered through a 0.22 micron filter (Millipore) and stored at 4° C. Sodium periodate causes oxidation of carbohydrate residues that contain vicinal hydroxyl groups. The N-linked oligosaccharides at all three glycosylation sites of rt-PA contain residues susceptible to periodate oxidation. The neutral and amino sugar compositions of rt-PA and periodate-treated rt-PA are shown in Table 2. As expected, the fucose were completely destroyed by the action of periodate. The drop in mannose content was consistent with the destruction of the terminal residues of the high-mannose oligosaccharide at position 117 and the 2-linked residues of the complex oligosaccharides at positions 184 and 448. Some decrease in galactose levels was also observed, presumably as a result of oxidation of terminal galactose moieties (i.e., those not substituted with sialic acid).

Amino acid analysis without reduction and carboxymethylation demonstrated that cysteine residues were not oxidized to cysteic acid by the periodate treatment. After reduction and carboxymethylation, 34.2 nmoles (expected number is 35) of carboxymethyl cysteine per nmole of rt-PA were recovered in the periodate-treated sample. Recovery of methionine in the periodate-treated rt-PA was only 0.9 nmoles out of 5.0; untreated rt-PA had a value of 2.5 nmoles. However, with reduction and carboxymethylation, methionine recoveries increased to 3.3 and 2.8 nmoles for the periodate-treated and untreated materials respectively. These results may suggest the presence of methionine sulfoxide in the treated sample. There was no significant difference in recovery of the other amino acids between the periodate-treated and untreated rt-PA (data not shown). Treatment with periodate did not alter the activity of the rt-PA significantly. The specific activity of the periodate-treated rt-PA was 91% that of the control rt-PA as measured by an in vitro clot lysis assay (Collen, D. et al., J. Clin. Path. 21:705–707 [1968]).

EXAMPLE 7

High Mannose t-PA Variant

Chinese hamster ovary clone 15B cells (Gottleib, C. et al., J. Biol. Chem. 250:3303–3309 [1975]) are cotransfected with a plasmid encoding tissue plasminogen activator and dihydrofolate reductase pETPFR described in European Publication No. 093619 and pSVENEOBa16 (European Publication No. 160457) expressing a protein to convey neomycin resistance. Clone 15B is a CHO cell mutant lacking the enzyme N-acetylglucosamine transferase I (Gottleib, C. et al., supra). Cotransfection into CHO 15B cells is by modification of the calcium phosphate coprecipitation technique of Graham and Van Der Eb (Graham, F. and Van Der Eb, A. Virology 52:456–467 [1973]). Plasmid DNA (2.5 µg) was calcium phosphate coprecipitated and introduced to 106 cell for 3 hours. The cells were subsequently treated with 20% glycerol for 60 seconds and then fed with nonselective media. After 2 days the cells were passaged and fed with selective media (Ham F12-DMEM containing G418). Cells were grown for three weeks and then passaged into four 60 nm dishes. Upon reaching 80% confluency, the cells were fed another selective media (Ham F-12 DMEM containing 0, 50, 100 or 250 nM methotrexate). After two weeks, the cells were cloned into 96 well dishes by limiting dilution. Individual wells were assayed for rt-PA by Enzyme Linked Immunosorbent Assay (ELISA). Wells producing rt-PA were grown to confluency in 24 well dishes and amplified further with 500, 1000, 3000 and 10,000 nM methotrexate. One clone amplified to 3,000 and 10,000 nM methotrexate was selected and expanded for production of the mutant rt-PA. The rt-PA was purified using zinc chelate sepharose (chelating sepharose, Pharmacia) and an immobilized rabbit polyclonal antibody raised against wild type rt-PA. A specific activity similar to wild type rt-PA was determined using a chromogenic substrate S2251 (Kabi) and a polyclonal based ELISA.

A sample of rt-PA with high mannose oligosaccharides at all three glycosylation sites was prepared by expressing the gene for t-PA in CHO 15B cell line. The 15B cell line lacks the glycoprotein processing enzyme N-acetylglucosamine transferase I and, as a result, cannot synthesize complex type N-linked oligosaccharides. The neutral and amino sugar compositions of rt-PA produced in the 15B cell line were consistent with the presence of high mannose oligosaccharides at all three glycosylation sites (Table 2).

TABLE 2

| Carbohydrate Composition of Modified rt-PA | | | | |
|---|---|---|---|---|
| | Residue[a] (mole/mole rt-PA) | | | |
| | Fuc | Man | Gal | GlcNAc |
| Endo H[b] | | | | |
| control | 2.4 | 9.1 | 4.5 | 7.1 |
| treated | 2.2 | 3.5 | 4.5 | 6.2 |
| Periodate[c] | | | | |
| control | 2.2 | 9.2 | 3.6 | 8.9 |
| treated | — | 4.4 | 1.9 | 8.9 |
| High Mannose Mutant[c] | 1.5 | 16.2 | 0.9 | 6.0 |

[a]Abbreviations;

TABLE 2-continued

Carbohydrate Composition of Modified rt-PA

| | Residue[a] (mole/mole rt-PA) | | | |
|---|---|---|---|---|
| | Fuc | Man | Gal | GlcNAc |

Fuc = fucose,
Man = mannose,
Gal = galactose,
GlcNAc = N-acetylglucosamine.
[b]Normalized on galactose
[c]Normalized on GlcNAc

EXAMPLE 8

Pharmacokinetics of Tissue-type Plasminogen Activator Variants

Figure 4:
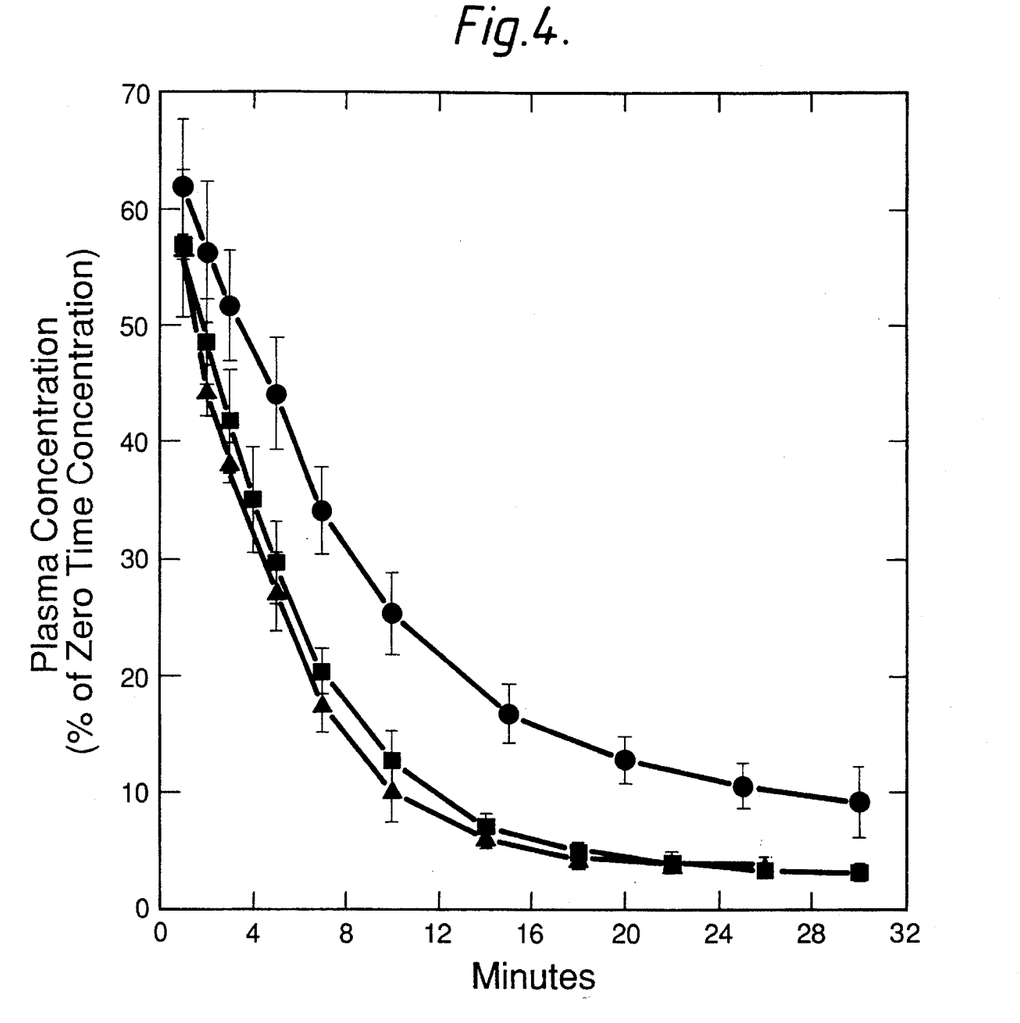
FIG. 4. Plasma concentration time course of control rt-PA (Δ) and rt-PA modified with sodium periodate (0) or Endo H (●). Data are presented as the mean ± standard deviation.
Figure 8:
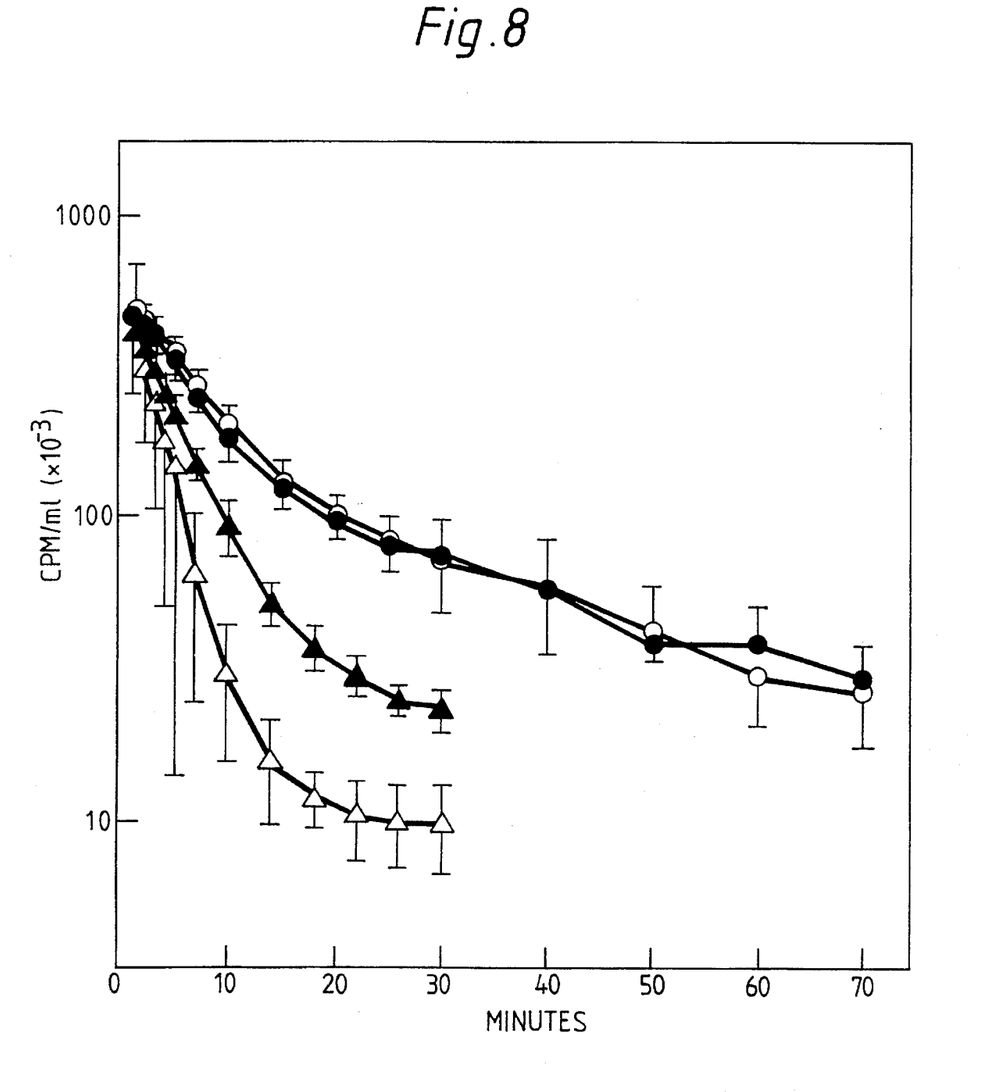
FIG. 8. Plasma concentration time course of $^{125}$I labeled high mannose rt-PA (Δ), control rt-PA (▲), Endo H treated rt-PA (0) and periodate treated rt-PA (●). Data are presented as mean ± standard deviation.

The plasma time courses of the Endo H and periodate modified forms of rt-PA are shown in FIG. 4. Both treatments appear to slow the elimination of rt-PA. There was a significant increase in the $t_{1/2}$ alpha for only the periodate treated rt-PA. Both Endo-H and periodate treated rt-PA had slower rates of clearance than control rt-PA, with 1.9 and 2.7-fold differences, respectively. The difference between the rate of clearance of Endo-H and periodate treated rt-PA was significant (P<0.005). There were no significant differences in $V_o$ or $t_{1/2}$ beta (Table 3).

periodate treated rt-PA were labeled and their pharmacokinetics were determined. The labeled rt-PA was always coinjected with 1 mg/kg of unmodified rt-PA. The patterns of elimination of the TCA precipitable counts from these modified rt-PAs are shown in FIG. 8. The rt-PA with high mannose oligosaccharide structures at all glycosylation sites, produced in the CHO 15B cell line, was also included in this experiment. All four forms of rt-PA had similar initial volumes of distribution. As was shown in FIG. 4, the Endo-H and periodate treated rt-PAs have smaller rates of clearance than the control rt-PA; the dominant change in the elimination pattern of the Endo-H and Periodate treated rt-PA again appears to be in the relative size of the alpha and beta phase. The rate of clearance of the HM rt-PA was nearly two fold larger. The most substantial change in the clearance of the HM t-PA appears to be due to a decrease in the alpha phase half life (Table 5).

Figure 5:
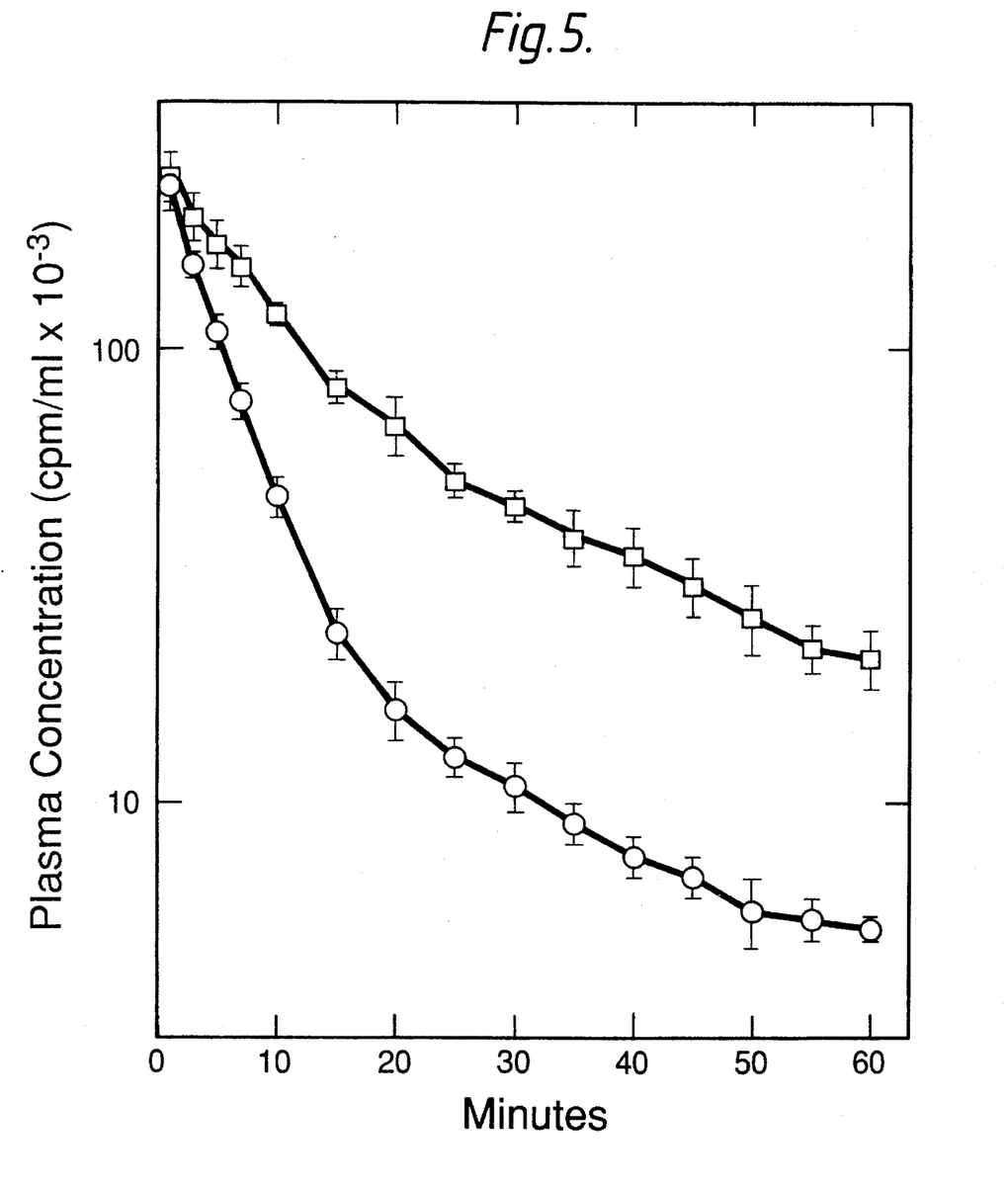
FIG. 5 represents a time course of the change of trichloroacetic acid (TCA) precipitable radioactivity for control human t-PA (0) and glutamine$_{117}$ t-PA (□).

The removal of the high mannose oligosaccharide at amino acid residue 117 by Endo-H and the oxidation by periodate appear to cause similar changes in pharmacokinetics. Consequently the Gln117 mutant was used as another tool to determine the role that the glycosylation at amino acid 117 might play in the elimination of rt-PA. FIG. 5 shows that this mutant behaves similarly to the other forms of rt-PA with slower elimination. The rate of clearance of Gln117 is more than 2-fold smaller than the control and there is a shift to a more prominent beta phase. No significant changes were seen in $V_o$, $t_{1/2}$ alpha and $t_{1/2}$ beta.

TABLE 3

Pharmacokinetics of unlabeled, modified and wild type rt-PA[a]

| rt-PA[b] | n | $V_o$ ml/kg | $T_{1/2}\alpha$ min | $T_{1/2}\beta$ min | % AUCα | % AUCβ | Cl ml/min/kg | $K_{10}$[c] | $K_{12}$ | $K_{21}$ |
|---|---|---|---|---|---|---|---|---|---|---|
| Control[b] | 5 | 43.2 | 2.61 | 19.6 | 82.0 | 18.0 | 9.57 | 227 | 35 | 42 |
| | | 13.0 | 0.29 | 2.0 | 18.7 | 5.2 | 1.87 | 30 | 2.6 | 4 |
| ENDO | 5 | 53.4 | 3.52 | 24.0 | 37.44** | 62.6** | 4.98** | 95** | 80** | 65 |
| | | 10.6 | 1.1 | 4.1 | 6.8 | 9.7 | 0.53 | 13 | 34 | 15 |
| Periodate | 5 | 56.4 | 4.22* | 37.5 | 29.7** | 70.3** | 3.53** | 63** | 72** | 54 |
| | | 10.4 | 0.77 | 10.9 | 7.7 | 11.4 | 0.57 | 6 | 22 | 20 |

[a]All data are presented with the mean over the standard deviation. If a significant difference (P < 0.05) was detected between groups by analysis of variance, a Student's t-test was done to determine the level of significance: (*) P < 0.05; (**) P < 0.01. The doses (mg/kg) for control, ENDO and periodate were 1.0, 0.83, adn 0.95, respectively.
[b]ENDO is rt-PA treated with Endo H. Periodate is rt-PA treated with sodium periodate.
[c]Microconstant $K_{10}$, $K_{12}$ and $K_{21}$ (min$^{-1}$ × 10$^3$).

Figure 7:
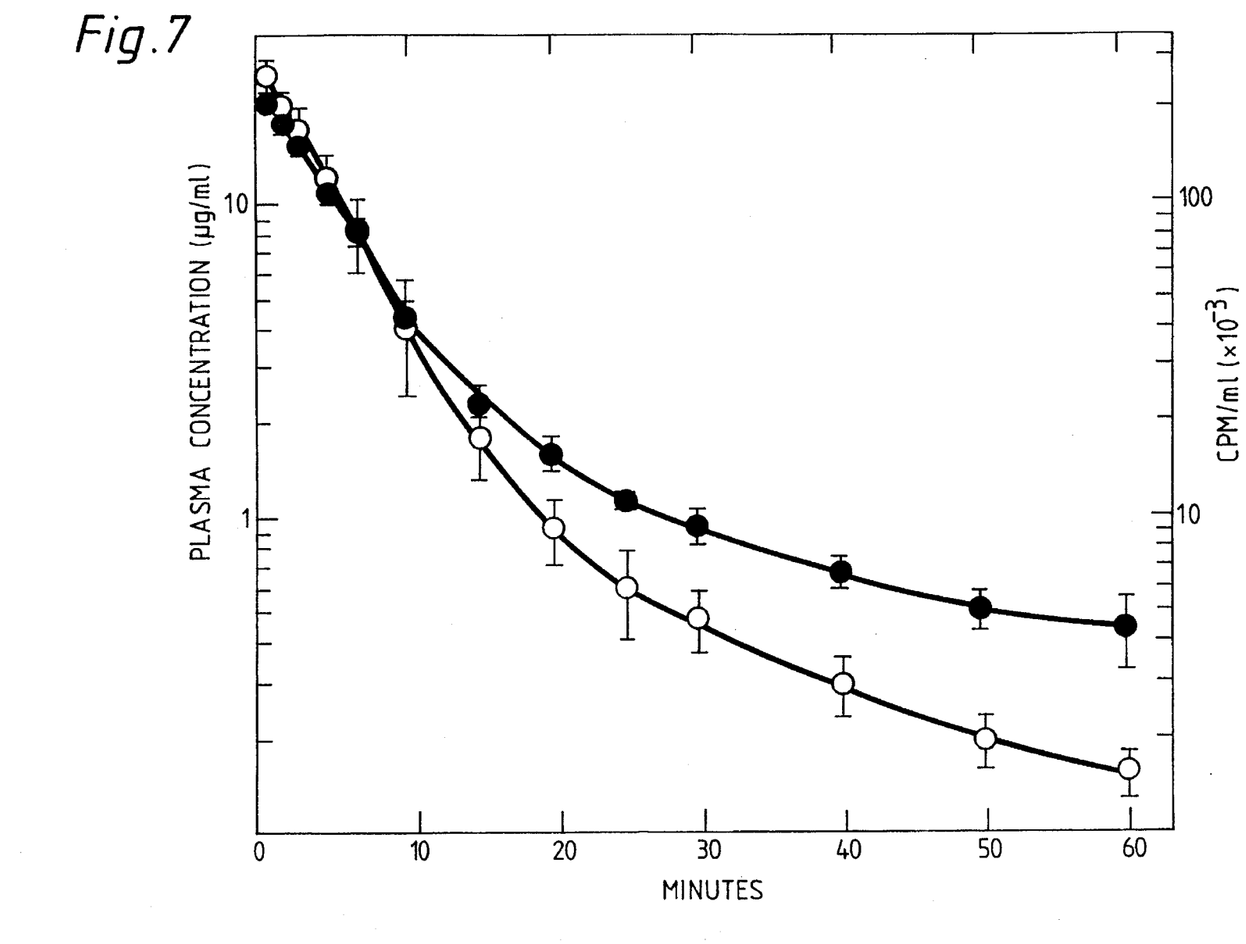
FIG. 7. Plasma concentration time course of $^{125}$I labeled (●) and unlabeled (0) control rt-PA. Data are presented as mean ± standard deviation.

The remaining modified forms of rt-PA were not available in quantities which would allow the pharmacokinetics to be characterized using the above techniques. Therefore the pharmacokinetic characteristics of these materials were determined following iodination. One limitation of this procedure is that the elimination of labeled and unlabeled forms of rt-PA is different (FIG. 7). The immunoreactivity and the TCA precipitable counts decrease in an identical pattern until approximately 90% of the unlabeled dose has been cleared. The curves then diverge with the labeled rt-PA being cleared more slowly. The pharmacokinetic parameters from these two curves are given in Table 4. Although the values of $V_o$, $t_{1/2}$ alpha and $t_{1/2}$ beta are not significantly different, the relative sizes of %AUCα and %AUCβ as well as the rate of clearance are significantly different.

In order to determine whether pharmacokinetic analysis with radiolabeled rt-PA could predict the differences in elimination which had been previously shown, Endo-H and

TABLE 4

Pharmacokinetics of labeled and unlabeled wild type rt-PA[a]

| rt-PA[b] | n | $V_o$ ml/kg | $T_{1/2}\alpha$ min | $T_{1/2}\beta$ min | % AUCα | % AUCβ | Cl ml/min/kg |
|---|---|---|---|---|---|---|---|
| IR | 4 | 30.0 | 21.3 | 3.05 | 81.5 | 18.5 | 5.51 |
| | | 3 | 2.0 | 0.42 | 14 | 3.2 | 0.85 |
| TCA | 4 | 27.7 | 30.3 | 3.36 | 62.1* | 37.9* | 3.92* |
| | | 1.9 | 9.5 | 0.28 | 7.2 | 5.5 | 0.40 |

[a]All data are presented with the mean over the standard deviation. (*) P < 0.01 by two tailed Student's t-test.
[b]Abbreviations are immunoreactive rt-PA (IR) and trichloroacetic acid precipitable radioactivity (TCA). The doses were 1 mg/kg and 3.4 μCi/kg for IR adn TCA, respectively.

TABLE 5

Pharmacokinetic parameters of labeled rt-PA treated with
Endo-H or periodate and high mannose rt-PA[a]

| rt-PA[b] | n | $V_o$ ml/kg | $T_{1/2}\alpha$ min | $T_{1/2}\beta$ min | % AUCα | % AUCβ | Cl ml/min/kg |
|---|---|---|---|---|---|---|---|
| Control | 5 | 31.5 | 2.55 | 14.9 | 52 | 48 | 5.72 |
|  |  | 8.5 | 0.66 | 3.8 | 5 | 6 | 0.45 |
| ENDO | 4 | 31.1 | 3.25** | 24.1 | 33** | 67** | 2.84** |
|  |  | 2.35 | 0.36 | 1.8 | 1.1 | 9 | 0.24 |
| Periodate | 4 | 32.6 | 3.30** | 30.3 | 32** | 68** | 2.74** |
|  |  | 2.3 | 0.49 | 3.7 | 3.1 | 7 | 0.25 |
| HM | 4 | 35.4 | 1.54** | 38.0* | 63** | 36* | 10.1** |
|  |  | 15.1 | 0.11 | 21.2 | 35 | 13 | 4.0 |

[a]All data are presented with the mean over the standard deviation. See Table 2 for the explanation of the statistical analysis.
[b]Control is wild type rt-PA; Periodate is rt-PA treated with sodium periodate; HM is high mannose rt-PA produced in the CHO-15B cell line; ENDO is rt-PA treated with Endo H. All doses were 10 μCi/kg.

The pharmacokinetics of glutamine$_{117}$ t-PA and control human t-PA are shown in FIG. 5. The glutamine$_{117}$ t-PA is cleared much more slowly than the control.

Figure 6:
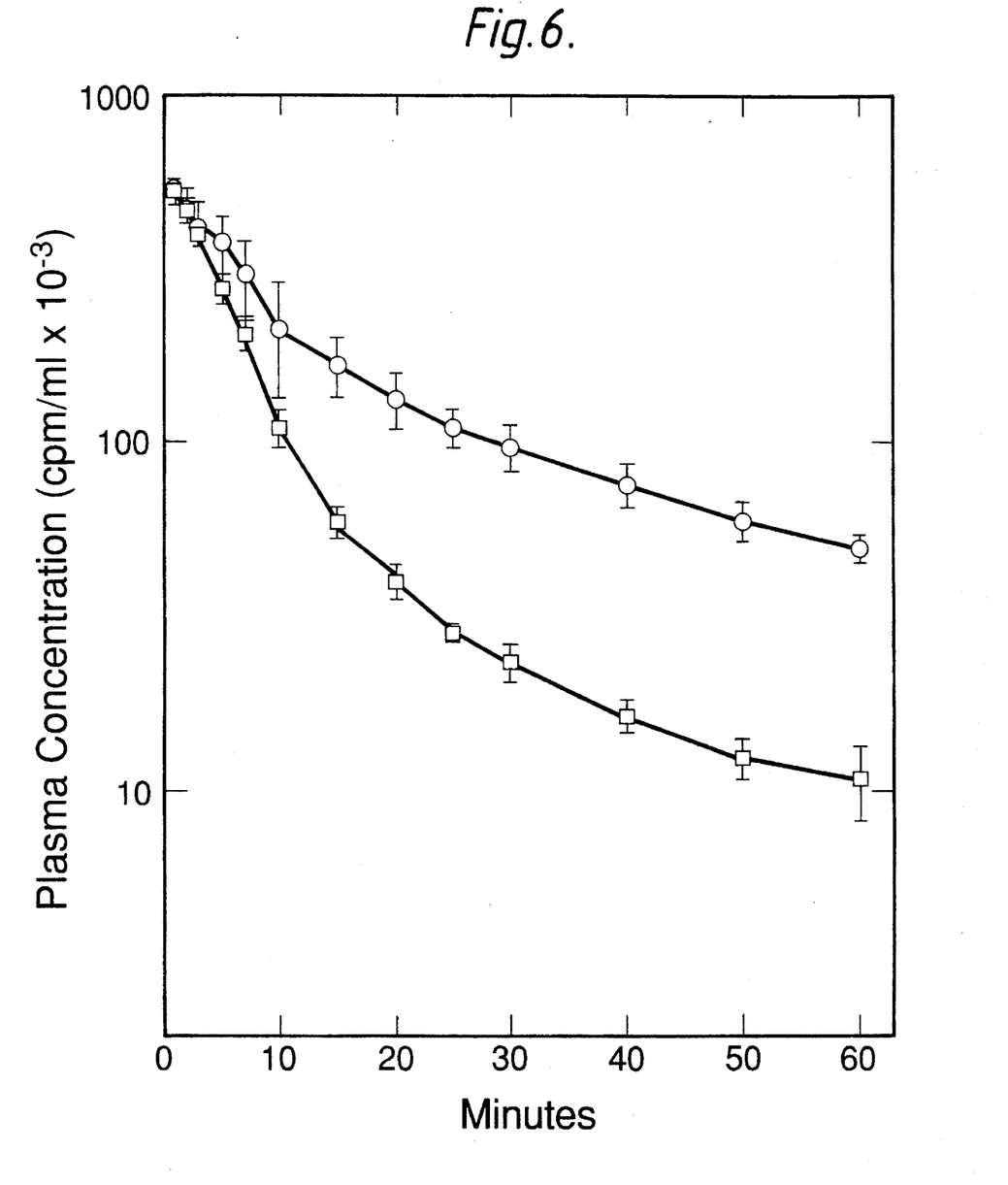
FIG. 6 represents a time course of the change of trichloroacetic acid (TCA) precipitable radioactivity for control human t-PA (□) and glutamine$_{117}$ glutamic acid$_{275}$ t-PA (0).

A similar profile is demonstrated by the glutamine$_{117}$glutamic acid$_{275}$ t-PA, prepared as described in Example 3, as shown in FIG. 6.

Fibrin Binding Characteristics

Fibrin binding is an extremely important factor which is presumably directly related to the fibrin specificity which human tissue-type plasminogen activator possesses in vivo. Fibrin binding of the Endo H human tissue-type plasminogen activator was evaluated by two procedures. The first procedure utilized the capture of human tissue-type plasminogen activator by fibrin coated on a well in a standard microtiter dish; each well is then washed and a solution of plasminogen and a chromogenic substrate for plasmin (S-2251, Kabi) is added. The color which is generated is proportional to the amount of human tissue-type plasminogen activator which is captured in the initial step (Angles-Cano, *Thrombosis and Haemostasis* 54, 171 (1985). The second type of assay for fibrin binding measures the quantity of human tissue-type plasminogen activator which is left in solution (by ELISA) when thrombin is added to a solution of plasminogen-free fibrinogen and human tissue-type plasminogen activator (Rijken et al, *J. Biol. Chem.* 257, 2920 (1982). It is presently unclear which assay adequately predicts the in vivo consequences of altered human tissue-type plasminogen activator fibrin binding. Based upon the data from each assay, we can conclude that Endo H-treated human tissue-type plasminogen activator has at least unchanged if not improved fibrin specificity.

Similarly, fibrin binding test data of glutamine$_{117}$ glutamic acid$_{275}$ t-PA, of Example 3, demonstrated that the glutamine$_{117}$ glutamic acid$_{275}$ t-PA is similar to glutamic acid$_{275}$ t-PA and is superior to t-PA control in fibrin stimulation and specific activity.

EXAMPLE 9

Fibrinolytic Activity of t-PA Variant Gln$_{117}$Met$_{119}$

The gln$_{117}$ and met$_{119}$ and mutants prepared as described in Examples 1 and 2 are each tested for fibrinolytic activity with similar results as with Endo H-treated material, as described above. The pharmacokinetics of each also are similar to those of Endo H- treated material, as compared with control human tissue-type plasminogen activators, as described above.

EXAMPLE 10

Pharmaceutical Compositions

The compounds of the present invention can be formulated according to known methods to prepare pharmaceutically useful compositions, whereby the human tissue-type plasminogen activator product hereof is combined in admixture with a pharmaceutically acceptable carrier vehicle. Suitable vehicles and their formulation, inclusive of other human proteins, e.g., human serum albumin, are described for example in Remingtont's *Pharmaceutical Sciences* by E. W. Martin, which is hereby incorporated by reference. Such compositions will contain an effective amount of the protein hereof together with suitable amount of vehicle in order to prepare pharmaceutically acceptable compositions suitable for effective administration to the host.

For example, the human tissue-type plasminogen activator hereof may be parenterally administered to subjects suffering from cardiovascular diseases or conditions. Dosage and dose rate may parallel that currently in use in clinical investigations of other cardiovascular, thrombolytic agents, e.g. about 1–2 mg/kg body weight as an intravenous or intra-arterial dose over 1.5–12 hours in patients suffering from myocardial infarction, pulmonary embolism, etc.

As one example of an appropriate dosage form, a vial containing 50 mg human tissue-type plasminogen activator, arginine, phosphoric acid and polysorbate 80 may be reconstituted with 50 ml sterile water for injection and mixed with a suitable volume of 0.9 percent Sodium Chloride Injection.

The extended or reduced half-life human tissue-type plasminogen activator may be suitable for rapid i.v. injection. This would eliminate the need for complex administration procedures and may increase the opportunity for the use of t-PA in settings with limited medical equipment such as in emergency vehicles staffed with paramedic personnel. An extended half-life of human tissue-type plasminogen activator may also allow lower, safer initial doses and could maintain thrombolytically effective plasmin levels for up to 45 minutes or longer. A longer half-life of human tissue-type plasminogen activator may also be useful for low dose extended therapy which may be necessary to avoid reocclusion following successful acute thrombolysis or for extended thrombolysis which may be necessary in cases of peripheral vascular occlusion. A reduced half-life of human tissue-type plasminogen activator may in certain patients be the desired type of thrombolytic therapy by providing effective plasmin levels over a shortened period of time.

Although the foregoing refers to particular preferred embodiments, it will be understood that the present invention is not so limited. It will occur to those ordinarily skilled in the art that various modifications may be made to the disclosed embodiments and that such modifications are intended to be within the scope of the present invention.

We claim:

1. A method for producing a human tissue-type plasminogen activator comprising transforming with DNA encoding said plasminogen activator variant mammalian host cell lacking N-acetylglucosamine aminotransferase, culturing the transformed cell, and recovering said variant from a culture of the cells.

2. A human tissue-type plasminogen activator variant produced in a mammalian ceil lacking N-acetylglucosamine amintransferase having a reduced in vivo half-life wherein the carbohydrate structure is modified by substitution of high mannose oligosaccharides at amino acid positions 184 and 448.

* * * * *